(12) United States Patent
Jiang et al.

(10) Patent No.: US 10,080,490 B2
(45) Date of Patent: Sep. 25, 2018

(54) FLEXIBLE-WIRE TRACTION-TYPE CAPSULE ENDOSCOPE AND MANUFACTURE METHOD THEREOF

(71) Applicants: Bo Jiang, Guangdong Province (CN); Jianhui Zhang, Guangdong Province (CN)

(72) Inventors: Bo Jiang, Guangdong Province (CN); Jianhui Zhang, Guangdong Province (CN)

(*) Notice: Subject to any disclaimer, the term of this patent is extended or adjusted under 35 U.S.C. 154(b) by 153 days.

(21) Appl. No.: 14/779,558

(22) PCT Filed: Apr. 16, 2015

(86) PCT No.: PCT/CN2015/076739
§ 371 (c)(1),
(2) Date: Sep. 23, 2015

(87) PCT Pub. No.: WO2015/158277
PCT Pub. Date: Oct. 22, 2015

(65) Prior Publication Data
US 2016/0045104 A1    Feb. 18, 2016

(30) Foreign Application Priority Data

Apr. 16, 2014    (CN) .......................... 2014 1 0152601

(51) Int. Cl.
*A61B 1/00* (2006.01)
*A61B 1/273* (2006.01)
(Continued)

(52) U.S. Cl.
CPC .......... *A61B 1/273* (2013.01); *A61B 1/00006* (2013.01); *A61B 1/0011* (2013.01);
(Continued)

(58) Field of Classification Search
CPC ..................... Y10S 600/92; A61M 25/0116; A61B 1/0011; A61B 1/00156; A61B 1/00158;
(Continued)

(56) References Cited

U.S. PATENT DOCUMENTS

| 5,482,993 | A  | * | 1/1996 | Hiraoka  | ................. | C08F 32/04 |
|           |    |   |        |          |                   | 524/789 |
| 6,775,848 | B2 | * | 8/2004 | McGlothlin | ............... | C08J 5/02 |
|           |    |   |        |          |                   | 2/168 |

(Continued)

OTHER PUBLICATIONS

Minnesota Rubber & Plastics—Apr. 22, 2012 https://www.mnrubber.com/design_guide/2-13.html.*
(Continued)

*Primary Examiner* — Ryan Henderson
*Assistant Examiner* — Pamela F Wu
(74) *Attorney, Agent, or Firm* — WPAT, P.C., Intellectual Property Attorneys; Anthony King

(57) ABSTRACT

The present invention discloses a flexible-wire traction-type capsule endoscope and a manufacture method thereof, which mainly includes a capsule endoscope housed in a pockety body and leads out a flexible wire for traction. The manufacture method of the flexible-wire traction-type capsule endoscope includes steps of mold integrating, film coating, adhering, shaping, assembling, sealing and wire fixing. According to the present invention, a finished product of the flexible-wire traction-type capsule endoscope is prepared by assembling a conventional capsule endoscope with a processed pockety body, and finally sealing and fixing. The manufacturing technique of the product is simple and easy, raw materials used are natural without pollution and are cheap, and the processing procedure is easy to be automatized, i.e., the productivity is easy to improve; from the aspect of application, the flexible-wire traction-type capsule
(Continued)

endoscope has a small structure volume, is easy to swallow, and causes small negative reactions to patients.

1 Claim, 5 Drawing Sheets

(51) Int. Cl.
  *A61B 1/04* (2006.01)
  *A61B 1/06* (2006.01)
(52) U.S. Cl.
  CPC ...... *A61B 1/00018* (2013.01); *A61B 1/00032* (2013.01); *A61B 1/00128* (2013.01); *A61B 1/00137* (2013.01); *A61B 1/00142* (2013.01); *A61B 1/041* (2013.01); *A61B 1/0684* (2013.01); *A61B 1/00096* (2013.01)
(58) Field of Classification Search
  CPC ......... A61B 1/0016; A61B 1/01; A61B 1/041; A61B 1/273; A61B 1/2733; A61B 1/2736; A61B 1/31; A61B 5/6861; A61B 2562/162; A61K 9/2095
  USPC ......... 600/110–112, 114–115, 160–183, 300, 600/301–309; 604/95.01–95.05
  See application file for complete search history.

(56) References Cited

U.S. PATENT DOCUMENTS

2005/0020880 A1* 1/2005 Miyake .............. A61B 1/00142
　　　　　　　　　　　　　　　　　　　　　　　600/121
2005/0085697 A1* 4/2005 Yokoi ................... A61B 1/041
　　　　　　　　　　　　　　　　　　　　　　　600/160

OTHER PUBLICATIONS

Surface armor—Jul. 31, 2013 http://www.surfacearmor.com/products/protective-film-tape/.*

* cited by examiner

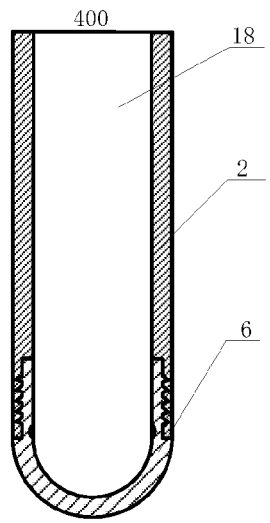
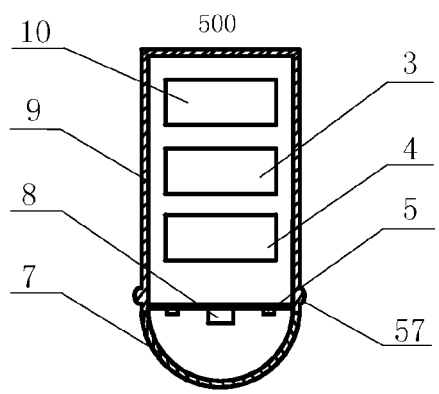
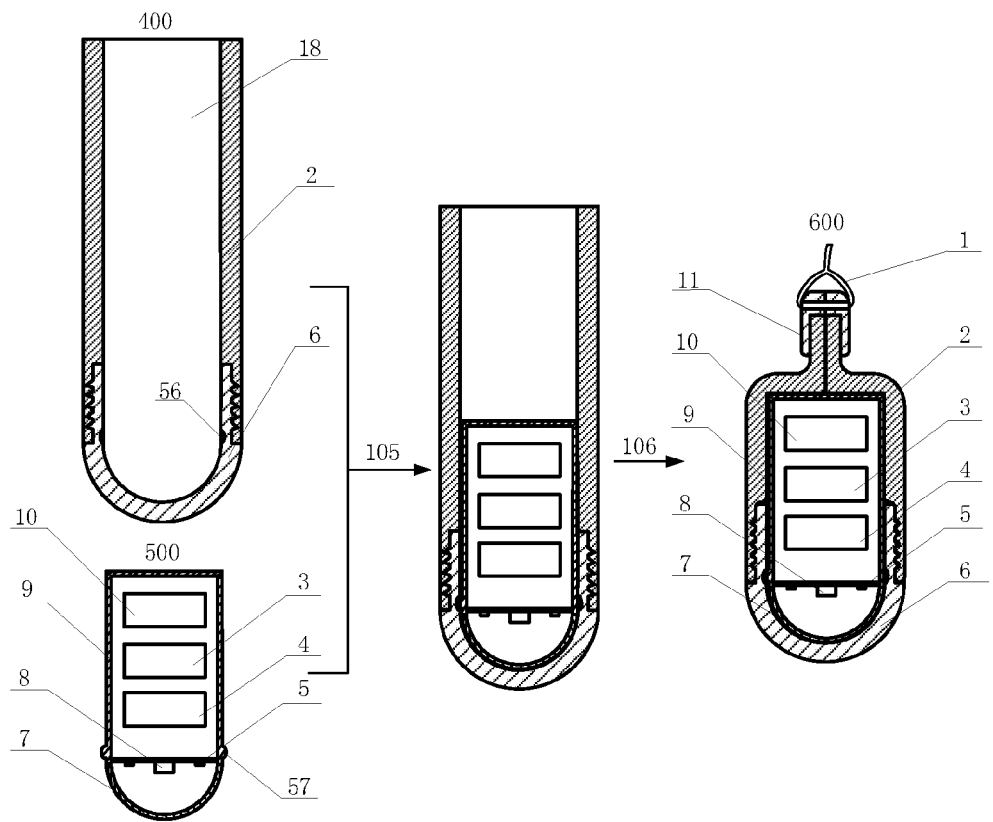
Fig. 7
Fig. 8
Fig. 9

FLEXIBLE-WIRE TRACTION-TYPE CAPSULE ENDOSCOPE AND MANUFACTURE METHOD THEREOF

TECHNICAL FIELD

The present invention relates to a capsule endoscope, and more particularly, to a capsule endoscope using a flexible wire for traction, and meanwhile, relates to a manufacture method of the capsule endoscope using the flexible wire for traction.

BACKGROUND

As a constituent of a digestive system, alimentary system lesions are very common, of which, esophagus cancer and stomach cancer are most severe. According to statistics, hundreds of thousands of people die of esophagus cancer and stomach cancer every year all round the world, with sickness rates and morbidity rates varying with each place. China is one of high-prevalence areas suffering esophagus cancer and stomach cancer; moreover, the sickness rate in rural area is far higher than that in an urban area. Clinic treatment results show that the esophagus cancer and the stomach cancer in the early stage can be cured; therefore, early detection is extremely important for reducing corresponding cancer incidence rate and lethality rate. Barium meal and endoscope are the main diagnostic methods at present, but these diagnostic methods are expensive, which are difficult to popularize widely in some remote areas. Moreover, the detection process is complicated to operate, which has a certain requirement on the technological level of the medical staff; secondly, the volumes of the existing endoscopes are generally big, which may cause injury to body organs during detection; meanwhile, the sufferer needs to bear the negative reactions caused by the endoscope during the entire detection process, which aggravates the sickness conditions of the sufferer.

With regard to the problems existing in a conventional alimentary system sickness detector, the medical staff tries to employ a medical wireless endoscope system (referred to as "capsule endoscope"). The capsule endoscope is a novel noninvasive indolent wireless detecting system, which is composed of a pill-like capsule for realizing digestive tube detection function and an in vitro image recorder. Because a micro-optical-electro-mechanical technology is employed, the smart endoscope has a very tiny size, and the sufferer does not need to be narcotized while swallowing it, and can move freely, thus avoiding pains and inconvenience brought by the conventional detection method. Because the technology contains significant business interests and application prospect, and has the advantages of simple operation, aponia and no cross infection or the like, the capsule endoscope is getting more and more attentions to researcher since at home and abroad.

However, there are still a lots of limitations for applying the conventional capsule endoscope in lesion detection. For example, the Patent No. 201220135353.3 titled as Capsule Endoscope discloses a capsule endoscope. The capsule endoscope is of a swallowing type, which is mainly applied to detect stomach, duodenum and lower digestive system diseases, and can move and be finally discharged in vitro under the gastrointestinal peristalsis. However, if the capsule endoscope is applied to detect an upper digestive system, particularly applied to an esophagus, it will be difficult to ensure the detection accuracy and reliability thereof. This is because that the capsule endoscope moves rapidly under the action of liquids in the esophagus or under the action of the gravitational force thereof, which is not relatively slow like that of gastrointestinal peristalsis. In this way, the staying time of the capsule endoscope in the esophagus cannot be ensured, which is just not beneficial for improving the detection accuracy and reliability. Moreover, in order to avoid cross infection, the capsule endoscope is a disposable product, thus causing that parts inside the capsule cannot be repeatedly used for many times, which causes wastes and improves the detection cost of the sufferer.

Therefore, in view of the technical problems existing in the capsule endoscope of the prior art, it needs to develop a novel capsule endoscope which can move and work flexibly, back and forth in the upper alimentary system, and implement accurate and controllable detection portion. Moreover, the capsule endoscope can be repeatedly used for multiple times, and cross infection can be avoided, so as to reduce the single-time detection cost of the sufferer, and relieve the workload of the medical staff.

SUMMARY

The present invention aims at solving the technical problem that the existing capsule endoscope cannot move and work flexibly, back and forth in the upper alimentary system, and implement accurate and controllable detection portion. Meanwhile, the present invention also provides a manufacture method of the capsule endoscope having this structure.

In order to solve the foregoing technical problem, the present invention provides a capsule endoscope using a flexible wire for traction, which includes a capsule endoscope, wherein the capsule endoscope includes an information receiving and processing device, a control circuit, a first optic window shade, an LED lamp bank disposed surrounding a CMOS lens, a rigid support and a drive power pack. The capsule endoscope is disposed in a pockety body, the first end of the pockety body is a second optic window shade corresponding to the position of the first optic window shade of the capsule endoscope, the second end of the pockety body is sealed through a bayonet connector and extends out of a flexible wire for traction, and a flexible housing is disposed between the first end and the second end of the pockety body; the lower edge of the rigid support is provided with at least one bulge, the outer edge of the upper end of the second optic window shade is provided with a dentate body, the lower edge of the second optic window shade is provided with recess, and the bulge is matched with the recess to assembly the capsule endoscope together with the pockety body. The body of the flexible-wire traction-type capsule endoscope according to the technical solution of the present invention is the capsule endoscope, which is integrated together with the pockety body via assembling; and one flexible-wire traction-type capsule endoscope can be manufactured by sealing the opening of the pockety body using the bayonet connector and leading out the flexible wire for traction.

The manufacture method for the flexible-wire traction-type capsule endoscope of the present invention includes the following steps of:

mold integrating step: taking a second optic window shade for interference fit with a rhoptry to prepare a first mold assembly, wherein the lower end of the rhoptry is housed at the opening end of a second optic window shade;

Film coating step: coating a layer of plastics film on the outer surface of the lower end of the second optic window shade to prepare a second mold assembly;

Adhering step: immersing the second mold assembly in a first vessel filled with natural liquid rubber to finish the growing of the prototype of a flexible housing, thus obtaining a pockety prototype assembly;

shaping step: immersing the pockety prototype assembly into a second vessel filled with hot aqueous ammonia, and solidifying the prototype of the flexible housing adhered on the second mold assembly under vulcanization, thus shaping the flexible housing; and disassembling the rhoptry and the plastic film at this moment to obtain a pockety body;

assembling step: making the capsule endoscope and the pockety body mutually clamped using cooperation between a bulge on a rigid support of a capsule endoscope and a recess of the second optic window shade on the pockety body; and Sealing and wire fixing step: sealing an upper end opening of the pockety body using a bayonet connector and fixing a flexible wire, thus obtaining a flexible-wire traction-type capsule endoscope.

According to the present invention, a finished product of the flexible-wire traction-type capsule endoscope is prepared by assembling a conventional capsule endoscope with a processed pockety body, and finally sealing and fixing. The manufacturing technique of the product is simple and easy, raw materials used are natural without pollution and are cheap, and the processing procedure is easy to be automatized, i.e., the productivity is easy to improve; from the aspect of application, the flexible-wire traction-type capsule endoscope has a small structure volume, is easy to swallow, and causes small negative reactions to patients. During detection, the flexible-wire traction-type capsule endoscope can reciprocate in the upper alimentary system as long as the flexible wire is lifted and pulled, thus accurately controlling the detection process, and being beneficial for improving the detection accuracy and reliability. Moreover, the detection process is extremely convenient to operate, which requires a relatively low technological level on the medical staff, and is easy to implement the popularization of the product. Moreover, when the flexible-wire traction-type capsule endoscope is used for detection, it can be dismounted after the detection to take the internal conventional capsule endoscope to implement multiple cycle use, thus reducing the use cost of the product and the detection cost of the sufferer.

BRIEF DESCRIPTION OF THE DRAWINGS

FIG. 7 is a structure schematic view of a pockety body;

FIG. 8 is a structure schematic view of a conventional capsule endoscope;

FIG. 9 is a schematic view of assembling, sealing and wire fixing steps by assembling a conventional capsule endoscope with the pockety body, sealing an upper end opening of the pockety body, and fixing a flexible wire to obtain a product.

Figure 1:
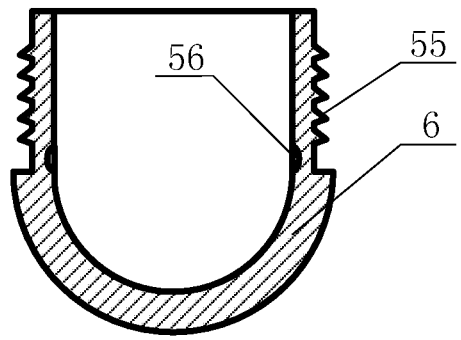
FIG. 1 is a structure schematic view of a second optic window shade.

Reference numerals and names in the Figs.: flexible cord 1, flexible housing 2, signal receiving and processing device 3, control circuit 4, LED lamp bank 5, second optic window shade 6, first optic window shade 7, CMOS lens 8, rigid support 9, drive power pack 10, bayonet connector 11, rhoptry 12, plastic film 13, first vessel 14, natural liquid rubber 15, second vessel 16, hot aqueous ammonia 17, upper end opening of pockety body 18, first mold assembly 100, second mold assembly 200, pockety prototype assembly 300, pockety body 400, conventional capsule endoscope 500, flexible-wire traction-type capsule endoscope 600, mold integrating step 101, film coating step 102, adhering step 103, shaping step 104, assembling step 105, and sealing and wire fixing step 106.

DETAILED DESCRIPTION

The present invention will be further described in details hereinafter with reference to the drawings.

First Embodiment

Figure 10:
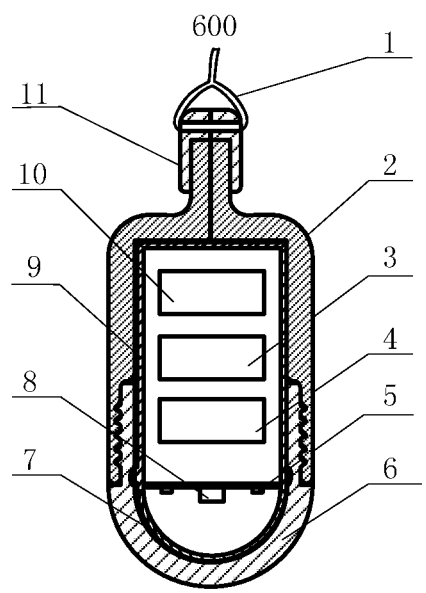
FIG. 10 is a structure schematic view of a flexible-wire traction-type capsule endoscope according to one embodiment.

The embodiment is a flexible-wire traction-type capsule endoscope 600, as shown in FIG. 1, FIG. 8 and FIG. 10, including a capsule endoscope 500, wherein the capsule endoscope includes an information receiving and processing device 3, a control circuit 4, a first optic window shade 7, an LED lamp bank 5 disposed surrounding a CMOS lens 8, a rigid support 9 and a drive power pack 10. The capsule endoscope 500 is disposed in a pockety body 400, the first end of the pockety body 400 is a second optic window shade 6 corresponding to the position of the first optic window shade 7 of the capsule endoscope, the second end of the pockety body 400 is sealed through a bayonet connector 11 and extends out of a flexible wire for traction 1, and a flexible housing 2 is disposed between the first end and the second end of the pockety body 400. The lower edge of the rigid support 9 is provided with at least one bulge 57, the outer edge of the upper end of the second optic window shade is provided with a dentate body 55, the lower edge of the second optic window shade is provided with recess 56, the bulge is matched with the recess 56 to assembly the capsule endoscope 500 together with the pockety body 400.

Second Embodiment

Figure 2:
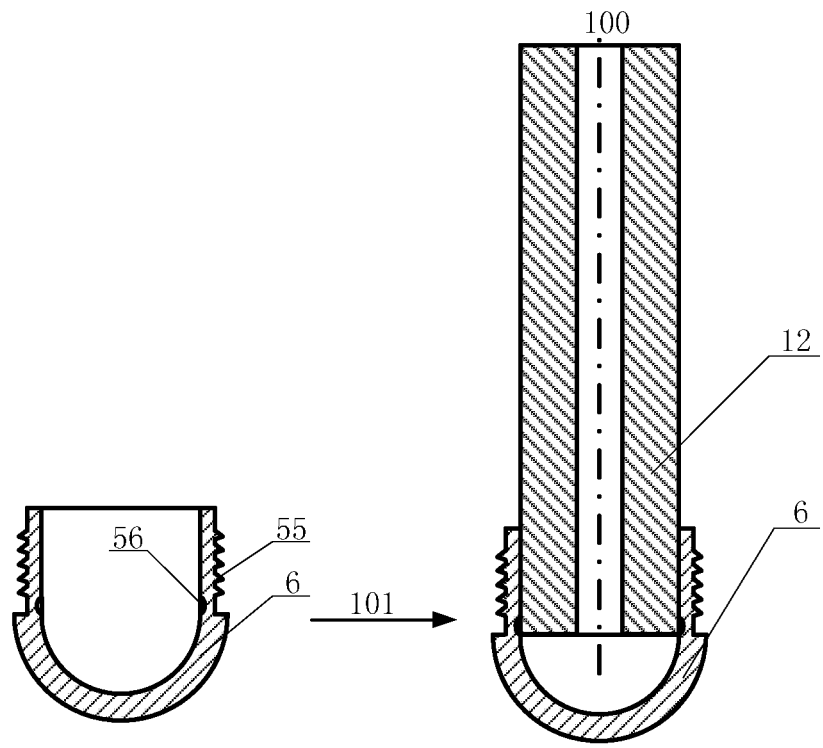
FIG. 2 is a schematic view of a mold integrating step, i.e., a step of taking the second optic window shade for interference fit with a rhoptry to prepare a first mold assembly.
Figure 3:
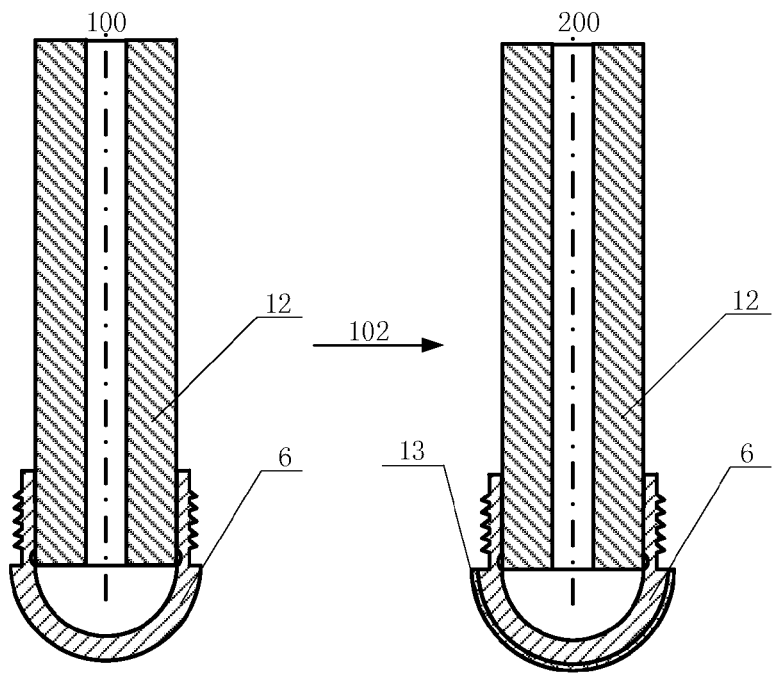
FIG. 3 is a schematic view of a film coating step, i.e., coating a layer of plastics film for protection on the outer surface of the lower end of the second optic window shade to prepare a second mold assembly.
Figure 4:
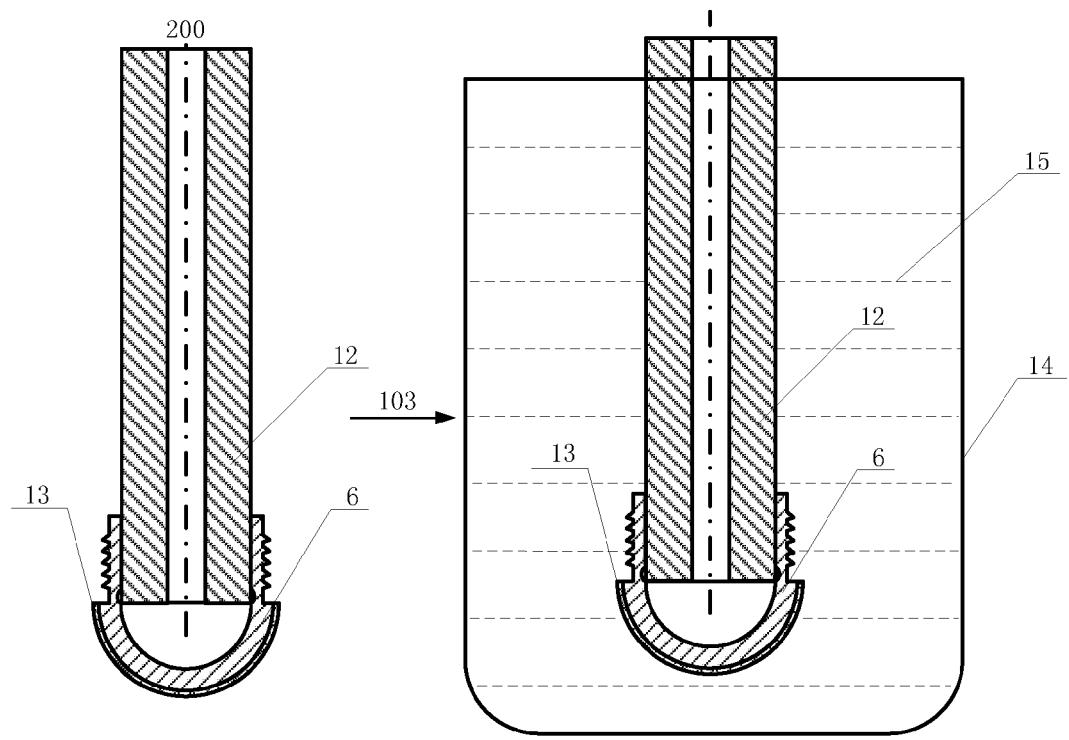
FIG. 4 is a schematic view of an adhering step, i.e., immersing the second mold assembly in a first vessel filled with natural liquid rubber to finish the growing of the prototype of a flexible housing.
Figure 5:
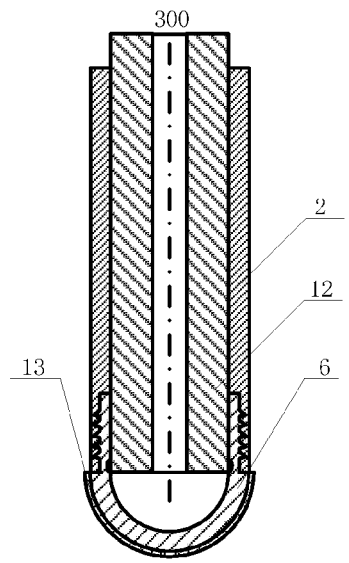
FIG. 5 is a structure schematic view of a pockety prototype assembly.
Figure 6:
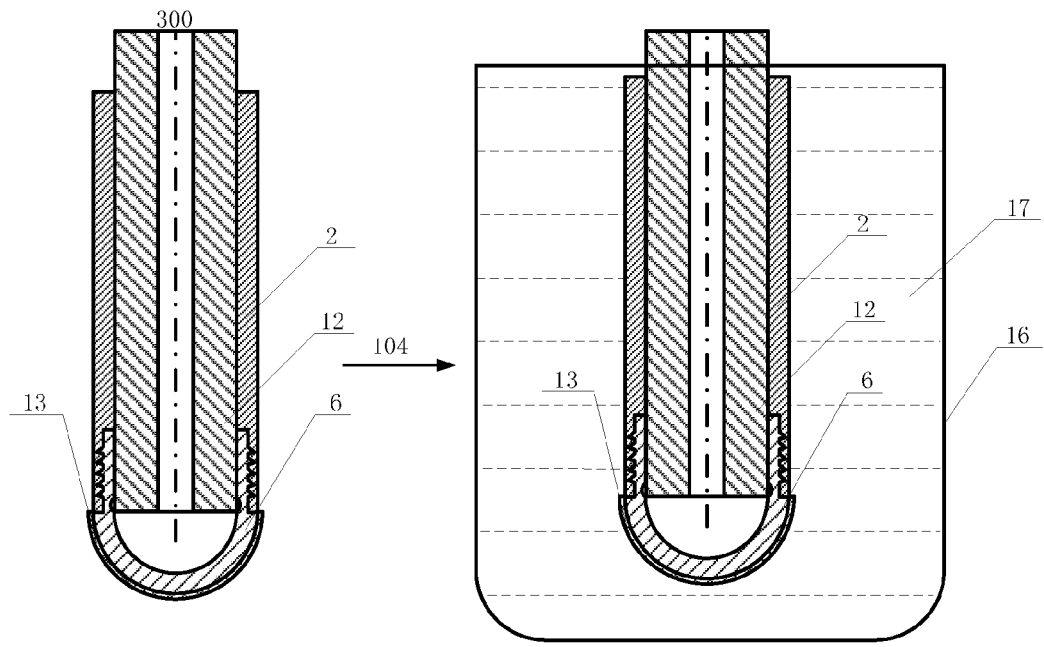
FIG. 6 is a schematic view of a shaping step, i.e., immersing the pockety prototype assembly into a second vessel filled with hot aqueous ammonia, and solidifying the prototype of the flexible housing adhered on the second mold assembly under vulcanization.

The embodiment is a manufacture method for a flexible-wire traction-type capsule endoscope, including the following steps of:

mold integrating step 101: as shown in FIG. 2, taking a second optic window shade 6 for interference fit with a rhoptry 12 to prepare a first mold assembly 100, wherein the lower end of the rhoptry 12 is housed at the opening end of a second optic window shade 6;

film coating step 102: as shown in FIG. 3, coating a layer of plastics film 13 on the outer surface of the lower end of the second optic window shade 6 to prepare a second mold assembly 200;

adhering step 103: as shown in FIG. 4, immersing the second mold assembly 200 in a first vessel 14 filled with natural liquid rubber 15 to finish the growing of the prototype of a flexible housing 2, thus obtaining a pockety prototype assembly 300 the structure of which is as shown in FIG. 5;

shaping step 104: immersing the pockety prototype assembly (300) into a second vessel (16) filled with hot aqueous ammonia (17), and solidifying the prototype of the flexible housing 2 adhered on the second mold assembly 200 under vulcanization, thus shaping the flexible housing 2; and disassembling the rhoptry 12 and the plastic film 13 at this moment to obtain a pockety body 400;

assembling step 105: as shown in FIG. 7, FIG. 8 and FIG. 9, making the capsule endoscope 500 and the pockety body 400 mutually clamped using cooperation between a bulge 57 on a rigid support 9 of a capsule endoscope 500 and a recess 56 of a second optic window shade 6 on the pockety body 400; and sealing and wire fixing step 106: as shown in FIG. 9, sealing an upper end opening 18 of the pockety body 400 using a bayonet connector 11, and fixing a flexible wire, thus obtaining a flexible-wire traction-type capsule endoscope 600.

The above only describes some implementations of the present invention. Those having ordinary skills in the art of the invention may also make many modifications and improvements without departing from the conceive of the invention which shall all fall within the protection scope of the invention.

The invention claimed is:

1. A manufacturing method for a flexible-wire traction-type capsule endoscope, comprising the following steps of:

a mold integrating step of taking a bar-shaped body to insert in a second optic window shade for preparing a first mold assembly, wherein a lower end of the bar-shaped body is housed at an opening end of the second optic window shade;

a film coating step of coating a layer of plastics film on an outer surface of the lower end of the second optic window shade to prepare a second mold assembly;

an adhering step of immersing the second mold assembly in a first vessel filled with natural liquid rubber to finish a prototype of a flexible housing on a dentate body of the outer edge of an upper end of the second optic window shade, thus obtaining a pockety prototype assembly;

a shaping step of immersing the pockety prototype assembly into a second vessel filled with hot aqueous ammonia, and solidifying the prototype of the flexible housing adhered on the second mold assembly under vulcanization, thus shaping the flexible housing; and disassembling the bar-shaped body and the plastics film after vulcanization to obtain a pockety body;

an assembling step of making a capsule endoscope and the pockety body being clamped together using cooperation between a bulge on a rigid support of the capsule endoscope and a recess of the second optic window shade on the pockety body; and a sealing and wire fixing step of sealing an upper end opening of the pockety body using a bayonet connector, and fixing a flexible wire to the bayonet connector, thus obtaining the flexible-wire traction-type capsule endoscope.

* * * * *